US006444453B1

(12) United States Patent
Lauf et al.

(10) Patent No.: US 6,444,453 B1
(45) Date of Patent: Sep. 3, 2002

(54) MIXED OXIDE NANOPARTICLES AND METHOD OF MAKING

(75) Inventors: Robert J. Lauf, Oak Ridge; Tommy J. Phelps, Knoxville, both of TN (US); Chuanlun Zhang, Columbia, MO (US); Yul Roh, Oak Ridge, TN (US)

(73) Assignee: Ut-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/428,376

(22) Filed: Oct. 28, 1999

(51) Int. Cl.$^7$ .................................................. C12P 3/00
(52) U.S. Cl. ...................................................... 435/168
(58) Field of Search .......................................... 435/168

(56) References Cited

PUBLICATIONS

Zhang et al "Formation of Magnetite and Iron–Rich Carbonats by Thermophilic Iron–Reducing Bacteria" SPIE vol. 3111 p. 61–68 1997.*

Dunin–Borkowski et al., "Magnetic microstructure of magnetotactic bacteria by electron holography", *Science*, 282:1868–1870, 1998.

Liu et al., "Thermophilic Fe(III)–reducing bacteria from the deep subsurface: The evolutionary implications," *Science*, 277:1106–1109, 1997.

Lovley, "Dissimilatory metal reduction," *Annu. Rev. Microbiol.*, 47:263–290, 1993.

Lovley et al., "Anaerobic production of magnetite by a dissimilatory iron–reducing microorganism," *Nature*, 330:252–254, 1987.

Nealson and Saffarini, "Iron and manganese in anaerobic respiration: Environmental significance, physiology, and regulation," *Annu. Rev. Microbiol.*, 48:311–343, 1994.

Rickard, "The microbiological formation of iron sulfides," *Stockholm Contrib. Geol.*, 20:49–66, 1969.

Perry et al., "Geology and stable isotope geochemistry of the Biwabik iron formation, Northern Minnesota". *Econom. Geol.*, 68:1110–1125, 1973.

Zhang et al., "Enhancement of Fe(III), Co(III) and Cr(VI) reduction at elevated temperatures and by a thermophilic bacterium," *Appl. Biochem. and Biotech.*, 57–58:923–932, 1996.

Zhang et al., "Physiochemical, mineralogical, and isotopic characterization of magnetite–rich iron oxides formed by thermophilic iron–reducing bacteria," *Geochimica et Cosmochimica Acta.*, 61(21):4621–4632, 1997.

Zhang et al., "Iron reduction by psychrothrophic enrichment cultures," *FEMS Microbiology Ecology*, 30:367–371, 1999.

* cited by examiner

*Primary Examiner*—Herbert J. Lilling
(74) *Attorney, Agent, or Firm*—Akerman, Senterfitt & Eidson, P.A.

(57) ABSTRACT

Methods and apparatus for producing mixed oxide nanoparticulates are disclosed. Selected thermophilic bacteria cultured with suitable reducible metals in the presence of an electron donor may be cultured under conditions that reduce at least one metal to form a doped crystal or mixed oxide composition. The bacteria will form nanoparticles outside the cell, allowing easy recovery. Selection of metals depends on the redox potentials of the reducing agents added to the culture. Typically hydrogen or glucose are used as electron donors.

27 Claims, 4 Drawing Sheets

MIXED OXIDE NANOPARTICLES AND METHOD OF MAKING

1.0 BACKGROUND OF THE INVENTION

This invention was made with Government support under Contract No. DE-AC05-96OR21400 awarded by the U.S. Department of Energy to Lockheed Martin Energy Research, Inc., and the Government has certain rights in this invention.

1.1 FIELD OF THE INVENTION

This invention relates to the field of ceramic processing. More particularly, this invention relates to a method for making fine particulates of ceramic powders through the reduction of selected ionic species by thermophilic bacteria

1.2 DESCRIPTION OF THE RELATED ART

In the production of ferrites and many other ceramics, mixed oxide powders are traditionally synthesized by mixing oxides, carbonates, etc., calcining at a high temperature, and milling to reduce particle size. The process is energy and time intensive, frequently hard to control, and sometimes must be done several times before the final product is obtained.

Also, there is a lower practical limit on the particle size that can be achieved by mechanical milling. Grinding ceramic materials to smaller sizes requires progressively more energy due to several reasons, including the greater difficulty in milling smaller particles that have fewer strength limiting defects than coarser particles. Additionally, grinding inefficiencies become significant because of mechanical aspects related to the transfer of useful energy from the milling medium to the particles and to fluid aspects related to the transport of particles through the grinding zone in the mill. Accordingly, for any given milling approach, the required milling time increases as the desired particle size decreases. Generally, contamination of the powder increases with increasing milling time because of abrasion of material from the medium.

Alternatively, chemical routes such as precipitation, sol-gel, and the like can be employed. These processes are generally more costly than calcining, but may yield a product with a higher level of chemical homogeneity and a very fine particle size. The precipitation of iron oxides by aqueous routes generally yields ferric oxide ($Fe_2O_3$), which must be reduced (by heating in hydrogen, for example) if a magnetic iron oxide ($Fe_3O_4$) is the desired product. This treatment adds more process steps, often including a milling step to break up agglomerates formed during the reduction process.

It has been known for some time that certain bacteria reduce Fe(III) in various geochemical environments. Microbial Fe(III) reduction has been observed primarily in low temperature environments that have been extensively influenced by modern surface biogeochemical processes such as weathering or microbial metabolism(Lovley, 1993; Nealson and Saffarini, 1994). It is also known that certain bacteria such as *Desulfovibrio desulfuricans* reduce sulfate to sulfide under anaerobic conditions (Rickard, 1969). The formation of some mineral deposits such as magnetite deposits in banded iron formations in both ancient and modern times may be attributed to the action of such bacteria.

Magnetotactic bacteria such as those described by Dunin-Borkowski, et al., (1998) form magnetic nanocrystals within the cell. However, the ratio of product nanocrystals to biomass is relatively low, typically a few nanocrystals per cell.

Several varieties of thermophilic bacteria such as Thermoanerobacter and Thermoanerobium are known to reduce Fe(III) ions as part of their respiration processes. These bacteria have been found in core samples from two geologically and hydrologically separated sedimentary basins, the Taylorsville Basin in Virginia and the Piceance Basin in Colorado. Both the Taylorsville and Piceance Basins have been isolated from surface processes for millions of years. The conditions under which the bacteria were found are summarized below in Table 1.

The differences in thermophiles found in hot springs in comparison with deep subsurface include environmental conditions such as pressure, nutrients and evolution. The actual differences between the microorganisms may be minor; however, thermophiles from hot springs have not yet been demonstrated to produce mixed oxides.

TABLE 1

| Locality | Taylorsville | Piceance |
| --- | --- | --- |
| Age | Triassic | Cretaceous |
| Depth (m) | 2652–2798 | 856–2096 |
| Temperature (° C.) | 65–85 | 42–85 |
| Pressure (Mpa*) | 30–35 | |

*Mpa, Megapascal, $10^6$ Pa

As described by Liu et al., (1997), the bacteria appear to utilize any of several electron donors such as formate, acetate, lactate, pyruvate, or hydrogen, provided that an electron acceptor such as amorphous Fe(III) oxyhydroxide is present. Fe(III) oxyhydroxide is evidently converted to magnetite by the bacteria as a byproduct of their respiration. Magnetite is formed outside the cells in copious amounts of single crystals of well defined size averaging about 60±20 nm, and morphology.

It is also known that thermophilic bacteria reduce other metal ions, notably Cr(VI), Co(III), Ni(III), Mn(IV), and U(VI), (see, for example, Zhang et al., 1996). These studies were directed to the use of thermophilic bacteria to remediate metal-contaminated water and were conducted in cultures in the presence of only a single metal species.

2.0 SUMMARY OF THE INVENTION

The present invention provides a method to directly produce a wide variety of nanoparticulate mixed oxides, particularly those that are useful in the preparation of ceramics. The method takes advantage of the natural ability of selected thermophilic bacteria to efficiently reduce metal ions in the presence of a suitable electron donor, thereby providing nanoparticulates uniquely suitable for producing mixed oxides as well as selected doped crystalline phases.

Finely divided mixed oxides are frequently used as ceramic colorants and glazes. The oxides of cobalt are particularly well known in these applications. Because the disclosed process can reduce Co(III) to Co(II), it can be adapted to the manufacture of various mixed oxides in which cobalt oxide is the major constituent. Added oxides such as those of Fe, V, Cr, Mn, and Zn may be incorporated to change the color behavior and/or refractoriness analogous to the additions of such dopants to $Fe_3O_4$ and $Cr_2O_3$. Numerous combinations of mixed oxides can be synthesized by this route, provided only that at least one of the metals in the process can be reduced from a first valence state to a second valence state through the respiration of the bacteria.

Another aspect of the present invention is an apparatus for producing a particulate. The apparatus includes a container and a solution in the container. The solution includes a first reducible metal, a second metal, and a bacterial culture. The bacteria reduce at least a portion of the first reducible metal to form the particulate. The particulate includes at least a portion of the first metal so reduced and at least a portion of the second metal which may or may not be reduced under the culture conditions.

The first metal used in the method or apparatus may include reducible transition metals, such as Fe(III), Cr(VI), Co(III), Ni(III), Mn(IV), U(VI), or other transition elements. The second or dopant metal may include reducible or non-reducible metals, such as Fe(III), Cr(VI), Co(III), Ni(III), Mn(IV), U(VI), Ni(II), Al(III), Zn(II), Mg(II), Mn(II), Cu(II), Co(II), or Pd(II). (The bacteria may comprise thermophilic bacteria.)

Bacteria for use in practicing the disclosed invention are selected from among thermophilic bacteria, preferably those that are typically grown and metabolize under conditions of elevated temperature, about 42° C.–65° C. Increased pressure may be used; however, the inventors find that under conditions of about 65° C. and normal atmospheric pressure conditions, mixed oxide particulates are efficiently produced.

3.0 BRIEF DESCRIPTION OF THE DRAWINGS

The invention may be better understood by reference to the following description taken in conjunction with the accompanying drawings, in which like reference numerals identify like elements, and in which.

4.0 DETAILED DESCRIPTION OF SPECIFIC EMBODIMENTS

Figure 1:
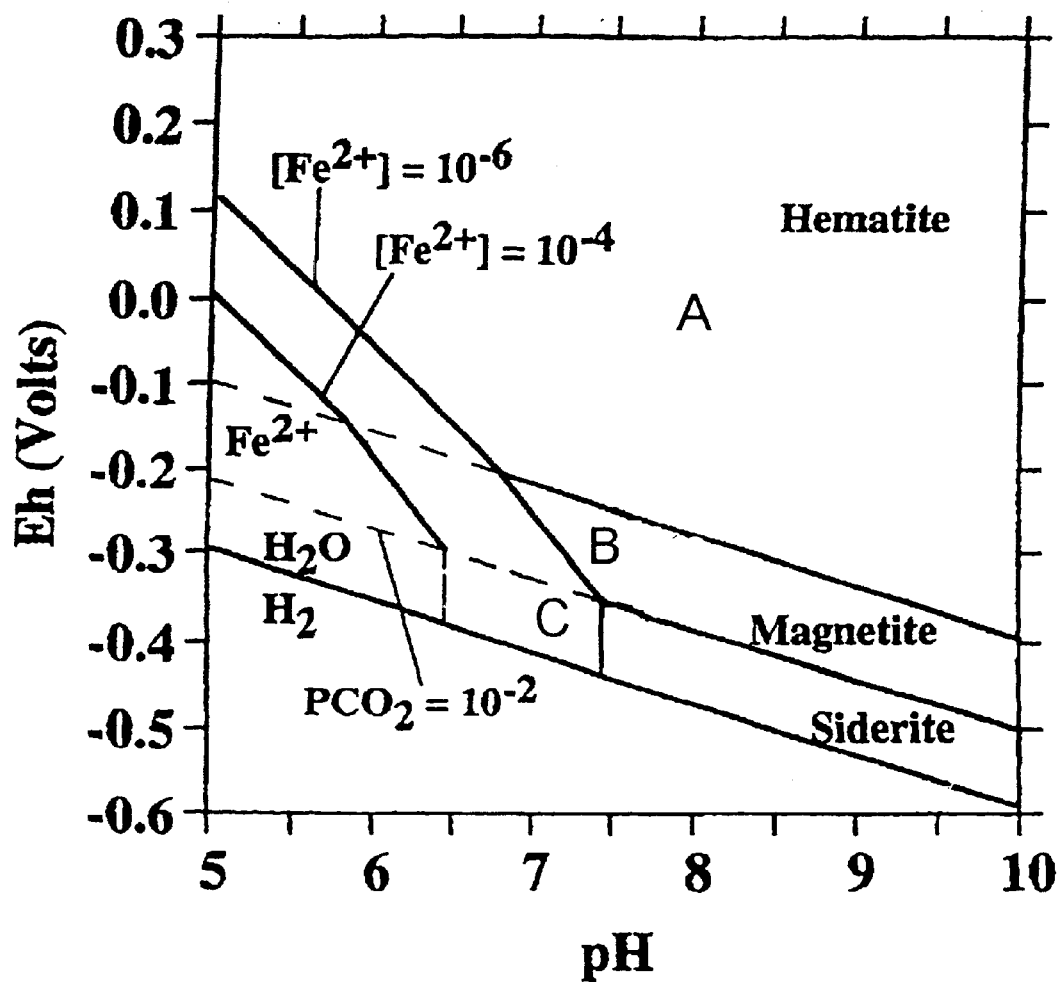
FIG. 1 is a redox potential-pH diagram illustrating regions of stability of various Fe-containing species and the electrochemical conditions established by thermophilic bacteria to facilitate the formation of magnetite.

While the invention is susceptible to various modifications and alternative forms, specific embodiments have been shown by way of example in the drawings and are described in detail. It should be understood, however, that the description of specific embodiments is not intended to limit the invention to the particular forms disclosed, but on the contrary, the intention is to cover all modifications, equivalents, and alternatives falling within the spirit and scope of the invention as defined by the appended claims.

Illustrative embodiments of the invention are described below. In the interest of clarity, not all features of an actual implementation are described in this specification. It will of course be appreciated that in the development of any such actual embodiment, numerous implementation-specific decisions must be made to achieve specific goals, such as compliance with system-related and business-related constraints, which will vary from one implementation to another. Moreover, such a development effort might be complex and time-consuming, but would nevertheless be a routine undertaking for those of ordinary skill in the art having the benefit of this disclosure.

4.1 Metal Oxide Reduction by Thermophilic Bacteria

The metabolic process in thermophilic bacteria which results in Fe(III) reduction generally involves a hydrogen electron donor and an iron Fe(III) acceptor. The hydrogen is split, yielding two hydrogen ions and two electrons. The two electrons pass through one or more metabolic processes within the bacterial cell, providing energy for the bacterium. The specific metabolic pathways have not been identified. Ultimately, two electrons are donated by the bacterial cell to a suitable electron acceptor such as Fe(III), reducing it to Fe(II) (Lovley et al., 1987).

Although the exact detailed steps of the mechanism by which thermophilic bacteria reduce ions is not known with certainty, the observed results may be placed into a thermodynamic context by considering the regions of stability of the various iron-containing species in a pH-potential plot (Pourbaix diagram) as shown in FIG. 1. For purposes of illustration, the discussion below focuses on the reduction of Fe(III); however, the concepts may be applied to other metal species.

Starting with an aqueous solution at pH of 8 and zero potential (Point A), any iron present will have a valence of +3, and a suspension of hydrous Fe(III) oxides will be stable. When thermophilic bacteria are added and provided with an electron donor source such as hydrogen, the hydrous Fe(III) oxides are converted to magnetite. One can see from the formula $Fe_3O_4$ that in the magnetite formed, ⅔ of the Fe ions are still Fe(III). Thus, it is theorized that the bacteria are not simply "reducing Fe(III) to Fe(II)" until it is used up, but are instead effectively moving the electrochemical potential of the system into the region where magnetite is the stable phase (Point B in FIG. 1). When all of the Fe(III) oxyhydroxide has been converted to magnetite, bacterial respiration ceases because the electrochemical potential of magnetite is such that it is not a usable electron acceptor in the bacterial system.

If one starts with a source of aqueous ferric ions such as FeO(OH) and adds an electron donor such as hydrogen (for example, by bubbling gaseous hydrogen through the solution) the equilibrium potential of the system initially lowers to some point generally indicated at Point C in FIG. 1. However, this only implies that the reaction:

$$3FeO(OH) + \tfrac{1}{2}H_2 \leftrightarrows Fe_3O_4 + 2H_2O \quad (1)$$

is thermodynamically favored. Kinetic limitations effectively prevent a significant amount of product to form this reaction from going forward at the temperatures ranging from ambient to about 65° C.

When iron-reducing bacteria are added, the reaction proceeds to completion with substantially all FeO(OH) being converted to $Fe_3O_4$. Thus, in a sense, the bacteria may be considered a catalyst that facilitates the kinetics of the above reaction. In contrast to a chemical catalyst, the bacteria extract some metabolic energy to survive, so the equilibrium potential of the entire assemblage is slightly higher than it would be with the electron donor present but no bacteria, as indicated by the relative positions of Points B and C. Point B remains within the region where $Fe_3O_4$ is the stable phase, but now the reaction shown in Equation 1 is also kinetically favorable because of the crucial role played by bacterial respiration in splitting the hydrogen molecule and making electrons available at a suitable potential to reduce Fe(III) and form $Fe_3O_4$. Similar reasoning may be applied to other electron donors such as lactate, pyruvate, formate, glucose, etc., for which overall reactions analogous to the one above can be written.

Figure 2:
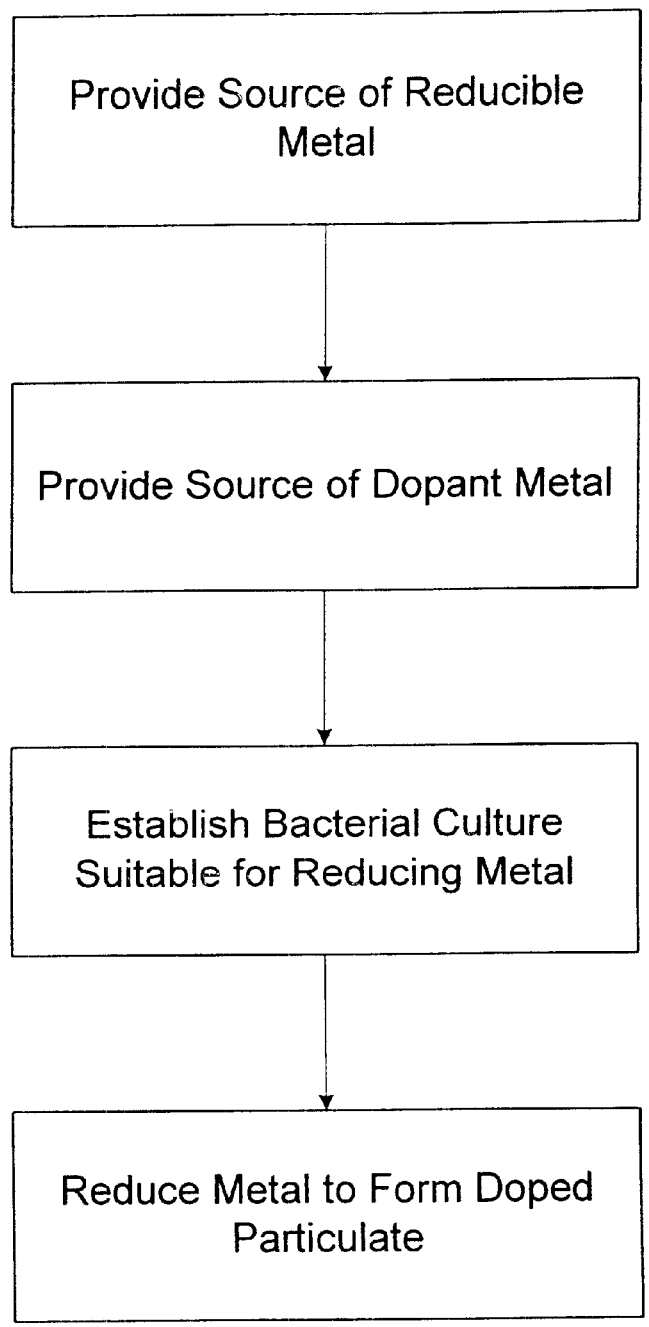
FIG. 2 is a process diagram illustrating a method for forming a mixed constituent crystalline phase in accordance with the present invention.

Referring to FIG. 2, a process diagram for forming a mixed constituent oxide is provided. A source of reducible metal is provided, and a source of at least one other dopant is provided. Bacterial cultures are established using bacteria suitable for reducing the metal in the presence of an electron donor. The dopant may or may not be reducible. The electron donor supports the metabolic pathway process of the bacteria that produces reduction of the metal. The bacteria reduce at least a portion of the metal to form a solid phase including at least a portion of the metal and the dopant. One or more dopants may be used and incorporated into the solid phase.

TABLE 2

| Bacterium | Locality/ Geological age | Lithology/ Depth | In-situ Temp. | Metals Reduced* | |
|---|---|---|---|---|---|
| Thermophilic/ TOR-39 | Taylorsville, Virginia/ Triassic | Sediments/ >2635 m Cr | 65– 85° C. 1997 | Fe, U, Mn, Co, Cr | Liu et al., |
| Thermophilic/ C1 | Parachute Pieance, Colorado/ Cretaceous | Sediments/ >840 m | 45– 85° C. | Fe, U, Mn, Co, Cr | Liu et al., 1997 |
| Thermophilic/ M3 | Parachute Pieance, Colorado/ Cretaceous | Sediments | 45– 85° C. | Fe, U, Co, Cr | Liu et al., 1997 |
| Psychrotrophic/ PV-1 | Hawaiian deep seawater/ modern | Iron-rich seawater | <5° C. | Fe, Co | Stapleton et al., 1999 |
| Psychrophilic/ W3-6-1 | Pacific deep marine sediments, Wecoma/ modern | Clay and Fine sand | <5° C. | Fe, Co | Stapleton et al., 1999 |
| Psychrophilic/ Ak-2 | Alaskan permafrost/ 6,000,000 yrs | Clay | <0° C. | Fe, Co | Stapleton et al., 1999 |
| Psychrophilic/ W3-7 | Siberian permafrost/ 4,000,000 yrs | Clay and Sand | <0° C. | Fe, Co | Zhang et al., 1999 |

*Batches made using glucose produced substantially all magnetite, whereas batches made with lactate or lactate/glucose mixtures produced mostly magnetite with a small amount of akaganeite in the final powders.

It is contemplated that a wide variety of electron acceptors may be used in the present invention. For example, transition elements, those with partially-filled d or f electron shells may be used. Also, elements that have partially-filled d or f shells in their commonly occurring oxidation states, such as the coinage metals, Cu, Ag, and Au may be considered transition elements for purposes of this illustration. All of these transition elements certain general properties in common, and may be subdivided into three main groups: the main transition elements, or d-block elements; the lanthanide elements; and the actinide elements.

The reduction potentials of several metals which the bacteria are expected to reduce are given below for illustration:

$Fe^{3+} + e^- = Fe^{2+}$      $E^0 = +0.77$ V
$UO_2^{2+} + 2H^+ + 2e^- = U^{4+} + 2H_2O$      $E^0 = +0.33$ V
$Co^{3+} + e^- = Co^{2+}$      $E^0 = +1.82$ V
$MnO_2 + 4H^+ + 2e^- = Mn^{2+} + 2H_2O$      $E^0 = +1.22$ V
$Cr_2O_7^{2-} + 14H^+ + 6e^- = 2Cr^{3+} + 7H_2O$      $E^0 = +0.33$ V

To implement the disclosed process, an anaerobic culture vessel is provided, containing an aqueous medium in which thermophilic bacteria are grown anaerobically. Additives such as vitamins, trace elements, and other nutrients are included in the culture medium. An electron donor such as hydrogen (80% balanced with $CO_2$), acetate (10 mM), lactate (40 mM), pyruvate (10 mM), formate (10 mM), glucose (10 mM), or other suitable source of biologically available electrons is added to the culture medium. A reducible metal acts as an electron acceptor and is added to the medium in the form of one or more transition metals (ions or solid phases) that can be moved from a first valence state to a second valence state upon accepting electrons from the anaerobic bacteria. When the transition metal is reduced, a crystalline product is formed external to the bacterial cells, typically as minute crystals. In the case where iron (e.g., in the form of Fe(III)) is used as the electron acceptor, the solid phase formed is magnetite. The dopant is incorporated into the magnetite crystals, thus forming doped magnetite.

Exemplary electron acceptor/dopant solutions are provided below in Table 3.

TABLE 3

| Acceptor (70 mM) | Dopant | Dopant Concentration |
|---|---|---|
| Fe(III) | Cobalt(III)-EDTA | 1, 4, 6, and 10 mM |
| Fe(III) | Cobalt(II) chloride | 1, 4, 6, and 10 mM |
| Fe(III) | Chromium(VI) | 0.4, 0.6, 0.8, and 1.0 mM |
| Fe(III) | Nickel(II) | 0.5, 1.0, and 1.5 mM |
| Fe(III) | Palladium(II) | 0.4, 0.6, 0.8, and 1.0 mM |

A systematic study was undertaken in which many experimental parameters were adjusted to determine the influence of different growth conditions and electron donors on the products formed, and on the overall efficiency of production. In these studies it was found, for example, that where hydrogen was used as the electron donor and Fe(III) was the electron acceptor, the magnetite powders formed were more uniform and had a finer particle size than when pyruvate is used as an electron donor. These studies also determined that maximum cell growth and Fe(III) reduction rates were obtained at about 65° C.

Specific examples are discussed in greater detail below. All bacteria in the following examples were grown in a basal medium containing the exemplary composition shown in Table 4.

TABLE 4

| Chemical | g/L |
|---|---|
| NaCl | 10 |
| $CaCl_2 \cdot 2H_2O$ | 0.1 |
| NH4Cl | 1.0 |
| $MgCl_2 \cdot 6H_2O$ | 0.2 |
| HEPES* | 7.2 |
| Yeast extract (composition not defined) | 0.5 |
| Vitamin solution | 1 mL |
| Trace mineral (see Table 5) | 10 mL |
| Resazurine (redox indicator) | 1 mL |

*($C_8H_{17}N_2O_4SNa$), N-[2-hydroxyethyl]piperazine-N'-[2-ethanesulfonic acid]

HEPES was used as a strong pH buffer because the thermophilic bacteria produce a large amount of organic acid during glucose fermentation which substantially lowers the pH. If the pH drops sufficiently, doped magnetite will not form effectively due to the higher proton concentration pushing the reduction equation in there reverse direction.

The components of the exemplary trace mineral solution are shown below in Table 5.

TABLE 5

| Chemical | g/L |
| --- | --- |
| nitrilotriacetic acid ($C_6H_9NO_6$) | 1.5 |
| $FeCl_2 \cdot 4H_2O$ | 0.2 |
| $MgCl_2 \cdot 6H_2O$ | 0.1 |
| Na tungstate ($Na_2WO_4 \cdot 2H_2O$) | 0.02 |
| $MnCl_2 \cdot 4H_2O$ | 0.1 |
| $CoCl_2 \cdot 6H_2O$ | 0.1 |
| $CaCL_2 \cdot 2H_2O$ | 1.0 |
| $ZnCl_2$ | 0.05 |
| $CuCl_2 \cdot 2H_2O$ | 0.002 |
| $H_3BO_3$ | 0.005 |
| $NaMoO_4 \cdot 2H_2O$ | 0.01 |
| NaCl | 1 |
| $Na_2SeO_3$ | 0.017 |
| $NiCl_2 \cdot 6H_2O$ | 0.024 |

Vitamins were provided by the exemplary solution shown in Table 6.

TABLE 6

| Vitamin | g/L |
| --- | --- |
| Biotin | 0.02 |
| Folic acid | 0.02 |
| B6(pyridoxine)HCl | 0.1 |
| B1(thiamine)HCl | 0.05 |
| B2(riboflavin) | 0.05 |
| Nicotinic acid (niacin) | 0.05 |
| Pantothenic acid | 0.05 |
| B12(cyanocobalamine) | 0.001 |
| PABA(p-aminobenzoic acid) | 0.05 |
| Lipoic acid (thioctic) | 0.05 |
| Distilled $H_2O$ | 1 L |

4.3 SUMMARY OF INVENTION AND UTILITIES

A large number of possible uses are contemplated for the particulate products. These include: microwave-absorbent materials and paints to suppress stray reflections on antenna structures; ceramic pigments; magnetic powders for recording media, xerographic toners, and magnetorheological media; and precursor materials for fabrication into magnets and other electronic devices.

The present invention involves advantageously using the respiration process of anaerobic bacteria, such as those described above, to manufacture nanocrystals for a variety of applications by the selective reduction of metal ions to form desired crystalline phases with mixed constituents, such as magnetite, maghemite, and other spinel compounds, as well as various other mixed oxides. Some typical applications for these nanocrystals include magnetorheological media, magnetic storage, dry printing, and magnetic devices.

The respiration process of the thermophilic bacteria effectively creates a nonselective source of electrons at an electrochemical potential that, in principle, is predictable to some degree. Culturing the bacteria with a mixture of transition metal electron acceptors yields a precipitate including a single-phase crystalline oxide containing this mixture of metals. In other words, with proper nutrients including Fe(III) and other transition metal ions, the bacteria can establish an Eh and pH where magnetite is stable, and the other transition metal ions are incorporated into the magnetite as it forms, thus yielding selectively doped ferrite materials. Generally, when producing a "doped" magnetite, the stability field for the doped magnetite should not be so different from that of "pure" magnetite that it cannot be reached by the potential imposed by the bacterial respiration process.

Ions such as Zn(II) may be incorporated into the growing magnetite even though the bacteria are not reducing the zinc ions, just as unreduced Fe(III) ions are incorporated into "undoped" magnetite. By analogous reasoning, those of ordinary skill in the art will appreciate that adding some Fe(III) to a culture in which the bacteria are reducing Cr(VI) to Cr(III) may yield an Fe-doped $Cr_2O_3$. Similarly, a mixture of Fe(III) and Cr(VI) in a 1:2 ratio may yield $FeCr_2O_4$. Hence, it can be seen that the inventive process may be used to create virtually unlimited combinations of mixed oxides.

Because the process used to form magnetite or doped magnetite described herein is performed at ambient or near ambient temperatures (<100° C.), unique ferrites that cannot be synthesized at all by calcining or other processes that take place at elevated temperatures (e.g., calcining of oxides or carbonates at 500° C.) may be formed. For example, many of the constituents of advanced ferrites can be either di- or trivalent, and the distribution of these is thermodynamically controlled. In particular, at higher temperatures, entropy effects will tend to encourage a distribution among +2 and +3 or between octahedral and tetrahedral sites. Making the compound at near ambient temperatures may encourage a sharper partitioning of certain species, e.g., Ni or Co, to certain sites. This could be especially important for products that use the magnetite in a powdered form that will not later be sintered (recording media, toner for xerographic copiers, etc.) because sintering would cause the partitioning of chemical species to revert to the high-temperature distribution.

Also, due to the low temperature process, the isotopic concentrations of certain ions, such as $^{18}O$, differ from the concentrations found in oxides formed using conventional methods, as shown in C. Zhang et al., (1997) These characteristic isotopic concentrations are useful in identifying products formed in accordance with the present invention.

5.0 EXAMPLES

5.1 Example 1

Production of Zinc(II) Doped Magnetite

This example illustrates that conditions can be established in a thermophilic bacterial culture in which a selected mixed oxide phase is thermodynamically stable. This stable phase allows incorporation of ions into a magnetite particulate regardless of whether or not the ions are themselves reduced by the bacteria. In the illustration, Zn(II) is originally present in the solution and remains in the +2 valence when incorporated into the structure of magnetite.

Doped magnetite was formed by a pure culture of bacteria strain TOR39 (Thermoanerobacter) growing on lactate as an electron donor. Freshly grown cultures were transferred into the basal medium (Table 4). Sterile amorphous Fe(III) oxyhydroxide (final concentration 70 mM) was added as the electron acceptor. Alternatively, sterile glucose (0.2% final concentration) could be employed as the electron donor. $H_2$ (80%, balanced with 20% $CO_2$) was added as an electron donor. Amorphous Fe(III) oxyhydroxide was formed by adding 0.4M $FeCl_3$ and 10M NaOH to precipitate the poorly crystalline precursor.

*Thernoanerobacter ethanolicus* strain TOR39 was deposited with the American Type Culture Collection (10801 University Blvd., Manassas, Va. 20010-2209) on Sep. 7, 2001 as accession number PTA-3695.

Anaerobic $ZnCl_2$ (final concentration 5 mM) was added as a dopant. The $ZnCl_2$ solution was flushed with $N_2$ gas and then autoclaved prior to microbiological use in order to remove dissolved oxygen. Incubation was at 65° C. for one week. Under these conditions, the bacteria produced a fine brown magnetic oxide powder. The solid material was washed three times with distilled water, dried under $N_2$, and stored in vacuum before analysis. Semiquantitative SEM/EDS analysis revealed that the powder contained Zn (estimated at several percent) and X-ray diffraction showed the material to be predominantly magnetite.

A thick layer of magnetic particles formed on the bottom of the vessel. The particulate product formed outside of the bacterial cell, allowing the product to be harvested without killing the bacteria. The ratio of product to biomass was approximately 85 g per 1 g dry weight of cells.

5.2 Example 2

Production of Cobalt Doped Magnetite

A batch was prepared using the same procedure as in Example 1 above, with the addition of anaerobic cobalt (III) EDTA (final concentration 1 mM) as a dopant. Incubation was at 65° C. for one week. A fine black powder was formed containing about 85 g magnetite in 8 L medium. The solid material was washed three times with anaerobic distilled water, dried under $N_2$, and stored in vacuum before analysis. The amount of Co in the final product was not determined. SEM/EDS analysis was inconclusive because of overlapping peaks; however, the material was strongly magnetic.

5.3 Example 3

Prodluction of Doped Ferrites

Additional experiments were conducted to demonstrate the growth of doped ferrites using several different compositions as shown below Table 7. All batches were made using bacterial strain TOR39 and yielded magnetite as the major phase after incubation at 65° C. The control experiments had no bacteria and the solid phase was akaganeite (i.e., no conversion to magnetite took place).

TABLE 7

| Sample | Electron Donor | Dopanat: Fe Ratio | Dopant source | Minerology (Major Phase)* |
|---|---|---|---|---|
| 1 | glucose | Co:Fe 6:70 | $CoCl_2$ | magnetite |
| 2 | glucose | Co:Fe 6:70 | Co(III)-EDTA | magnetite |
| 3 | glucose | Cr:Fe 0.6:70 | $K_2CrO_4$ | magnetite |
| 4 control | lactate | Co:Fe 6:70 | $CoCl_2$ | akaganeite |
| 5 | lactate | Co:Fe 4:70 | $CoCl_2$ | magnetite |
| 6 | lactate | Co:Fe 4:70 | $CoCl_2$ | magnetite |
| 7 | Lactate/glucose | Co:Fe 6:70 | $CoCl_2$ | magnetite |
| 8 | lactate | Co:Fe 6:70 | $CoCl_2$ | magnetite |
| 9 | lactate/glucose | Co:Fe 10:70 | $CoCl_2$ | magnetite |
| 10 | lactate | Co:Fe 10:70 | $CoCl_2$ | magnetite |
| 11 | lactate/glucose | Co:Fe 12:70 | $CoCl_2$ | magnetite |
| 12 | lactate | Co:Fe 12:70 | $CoCl_2$ | magnetite |
| 13 control | lactate | Co:Fe 6:70 | Co(III)-EDTA | akaganeite |
| 14 | lactate | Co:Fe 4:70 | Co(III)-EDTA | magnetite |
| 15 | lactate | Co:Fe 4:70 | Co(III)-EDTA | magnetite |
| 16 | Lactate/glucose | Co:Fe 6:70 | Co(III)-EDTA | magnetite |
| 17 | lactate | Co:Fe 6:70 | Co(III)-EDTA | magnetite |
| 18 | lactate/glucose | Co:Fe 10:70 | Co(III)-EDTA | magnetite |
| 19 | lactate | Co:Fe 10:70 | Co(III)-EDTA | magnetite |
| 20 | lactate/glucose | Co:Fe 12:70 | Co(III)-EDTA | magnetite |
| 21 | lactate | Co:Fe 12:70 | Co(III)-EDTA | magnetite |
| 22 control | lactate | Cr:Fe 0.6:70 | $K_2CrO_4$ | akaganeite |
| 23 | lactate | Cr:Fe 0.6:70 | $K_2CrO_4$ | magnetite |
| 24 | lactate | Cr:Fe 0.6:70 | $K_2CrO_4$ | magnetite |
| 25 | lactate | Cr:Fe 0.8:70 | $K_2CrO_4$ | magnetite |
| 26 | lactate | Cr:Fe 0.8:70 | $K_2CrO_4$ | magnetite |
| 27 | lactate | Cr:Fe 1:70 | $K_2CrO_4$ | magnetite |
| 28 | lactate | Cr:Fe 1:70 | $K_2CrO_4$ | magnetite |

Batches made using glucose produced substantially all magnetite, whereas batches made with lactate or lactate/glucose mixtures produced mostly magnetite with less than 10% of akaganeite in the product based on semiquantitative XRD analyses.

5.4 Example 4

Scale-up Processes

This example illustrates that the disclosed process can be scaled up easily by making a bioreactor of any desired size.

Scale-up experiments were conducted using 160 mL, 1000 mL, 2000 ml, 13.25 L, and 20 L serum bottles. Each batch was prepared using the same procedure as in Example 1 above, except that glucose (10 mM concentration) was substituted for hydrogen as the electron donor. The amounts of the various components were glucose:amorphous iron:innoculum:medium=1:5:2:50. Three samples from the 1000 mL bottles (two were doped with Co(III) to a final concentration of 1,4,6, and 10 mM and one with Cr(VI) to a final concentration of 0.4, 0.6, 0.8 and 1.0 mM yielded from 1.2 to 3 g of magnetite powder each.

After culturing for 22 days, the sample harvested from the 13.25 L bottle yielded about 85 g of magnetite powder after washing. One Cr-doped sample was analyzed by semiquantitative EDX and contained about 1–2% Cr. One sample of Co-doped magnetite was mounted in epoxy and polished in order to analyze the interiors of several particles by wavelength dispersive x-ray analysis. This analysis was done to confirm that the dopant was in fact incorporated into the crystallites and not merely adsorbed onto the surface of the crystals. Analysis showed approximately 0.3–0.5 at. % Co was present throughout the particle interiors, representing substitution for about 1% of the Fe in the magnetite structure.

Control samples (no bacteria present) were examined using XRD analyses. The mineral phase present was demonstrated to be akaganeite (FeOOH). Thus, no Fe(III) reduction had taken place in the absence of bacteria, and the batch did not produce magnetite. In these experiments, more efficient metabolism (faster growth rate) was observed using glucose instead of hydrogen as the electron donor and the rate of magnetite production was increased.

5.5 Example 5

Production of Fe(III) Doped Chromium Oxide

The disclosed process may be used with different combinations of mixed oxides, particularly for many potentially useful materials besides magnetite or other ferrites. In this example, $Cr_2O_3$ doped with Fe(III) was prepared. It is contemplated that small amounts of Al(III) can also be incorporated into $Cr_2O_3$ by a similar procedure.

A doped $Cr_2O_3$ material was prepared by adding dopant ions to a thermophilic TOR39 bacterial culture solution along with a source of hexavalent chromium. A source of Fe(III) and Cr(VI) were provided and and incubated to allow the bacteria to reduce the electrochemical potential to the point where $Cr_2O_3$ stably precipitated. Fe(III) became incorporated into this phase even though it had not been reduced.

In a 100 mL serum bottle, a culture was grown at 65° C. for four weeks using iron reducing medium, 10 mM glucose, 0.75 mM potassum chromate and 0.075 ferric citrate and using bacterial strain TOR39 Thermoanerobactor with glucose as the electron donor. A green powder precipitated in the culture within a week The precipitates formed through bacterial reduction of Cr(VI). $Cr_2O_3$ and $Fe_2O_3$ form a binary solid solution series the iron present was inferred to be incorporated into the $Cr_2O_3$ phase, because no magnetite was observed in the product.

5.6 Example 6

Batch Process Reactor

Figure 3:
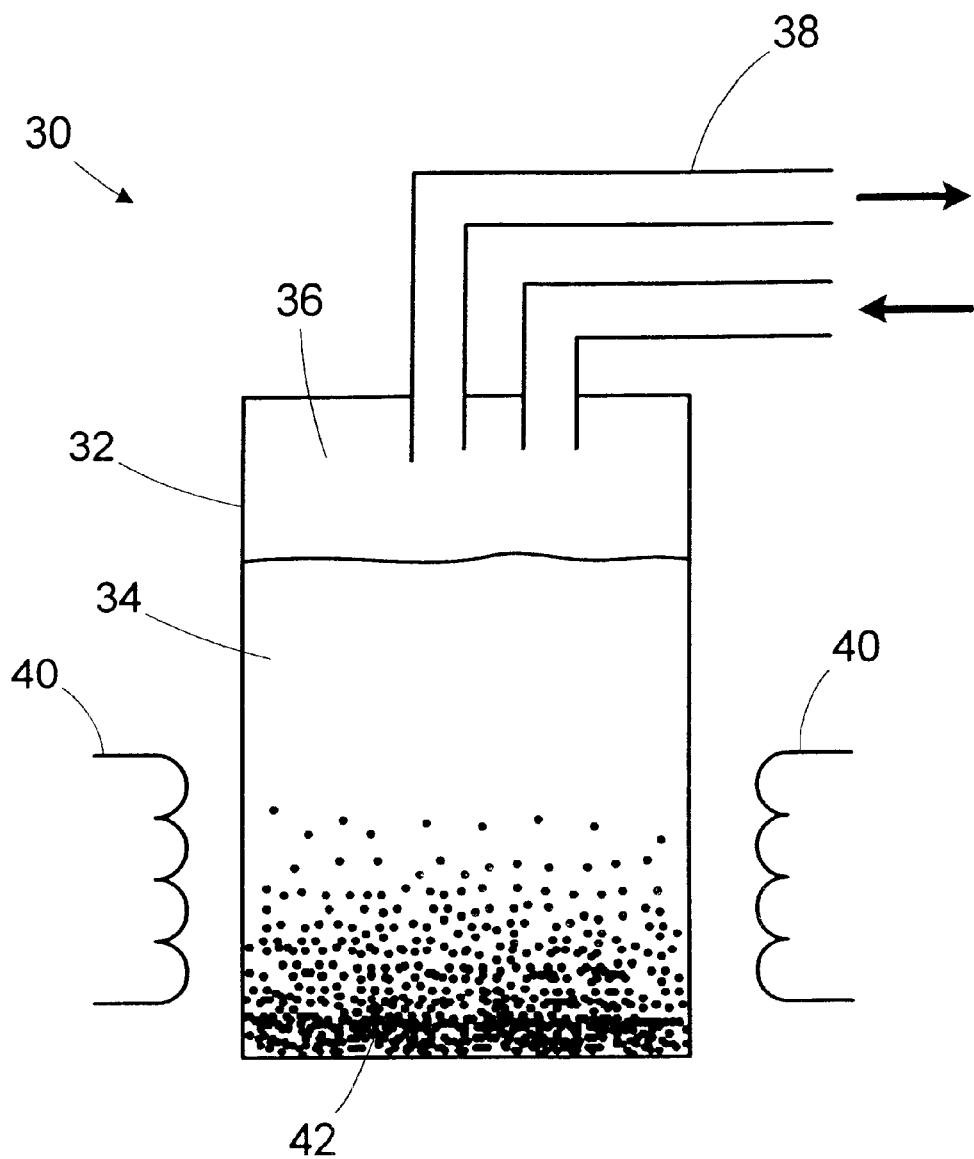
FIG. 3 illustrates a batch type reactor used to produce the mixed constituent crystalline phase.

FIG. 3 is a simplified diagram of a batch type bioprocessing reactor 30 suitable for carrying out the inventive process shown in FIG. 2. The reactor includes a container 32 constructed of glass or other inert material. A culture medium 34 is introduced in the container 32. The culture medium 34 contains an aqueous solution of nutrients, trace elements, vitamins, and other organic and inorganic compounds as described in the foregoing examples. The solutions described above are provided for illustrative purposes. Other solution constructs are possible, depending on the specific implementation.

The container 32 is sealed to prevent the entry of air into the headspace gas region 36 thereby maintaining anaerobic conditions within the culture as well as permitting the inventive process to be carried out at pressures greater or less than ambient if desired. A gas conduit 38 is included to allow the introduction of selected gases into the container and to allow gases to exit the container. A heating element 40 is provided proximate the container 32 to maintain the culture medium 34 at a desired temperature for growth of the anaerobic, thermophilic bacteria. An electron donor is introduced into the culture either as a gas (such as hydrogen or CO) through the gas conduit 38, or dissolved directly into the culture medium 34 in the case of simple organics such as glucose, lactate, and pyruvate. An electron acceptor is provided in the form of one or more reducible transition elements, such as Fe(III), Cr(VI), Co(III), Ni(III), Mn(IV), and U(VI), etc. dissolved in the culture medium 34. One or more additional dopant metal species, which may or may not be reducible are provided in the culture medium 34. If the dopant species is not reducible, for example Zn(II), it is generally present at a lower concentration than the reducible species. Exemplary dopant metals may include reducible or non-reducible metals, such as Fe(III), Cr(VI), Co(III), Ni(III), Mn(IV), U(VI), Ni(II), Al(III), Zn(II), Mg(II), Mn(II), Cu(II), Co(II), or Pd(II).

In a particular embodiment, the pH is maintained at a level between about 6.9 and 7.5, and the solution is maintained at a temperature of between about 45° C. and 75° C. Specific temperature and pH may be varied to optimize product yield, and the optimum values depend on factors including the particular mixed oxide being formed.

A crystalline product 42 forms in the container 32 as the bacteria reduces the reducible species. The dopant species is incorporated into the crystalline product 42, for example, $Fe_3O_4$, created through the reduction of the major metal species. When a sufficient quantity of crystalline product 42 has been produced and allowed to settle to the bottom of the container 32, the culture medium 34 is decanted and the crystalline product 42 is collected and washed. The incubation may be between 3 and 30 days, depending on the amount and size of the crystalline product desired.

Figure 4:
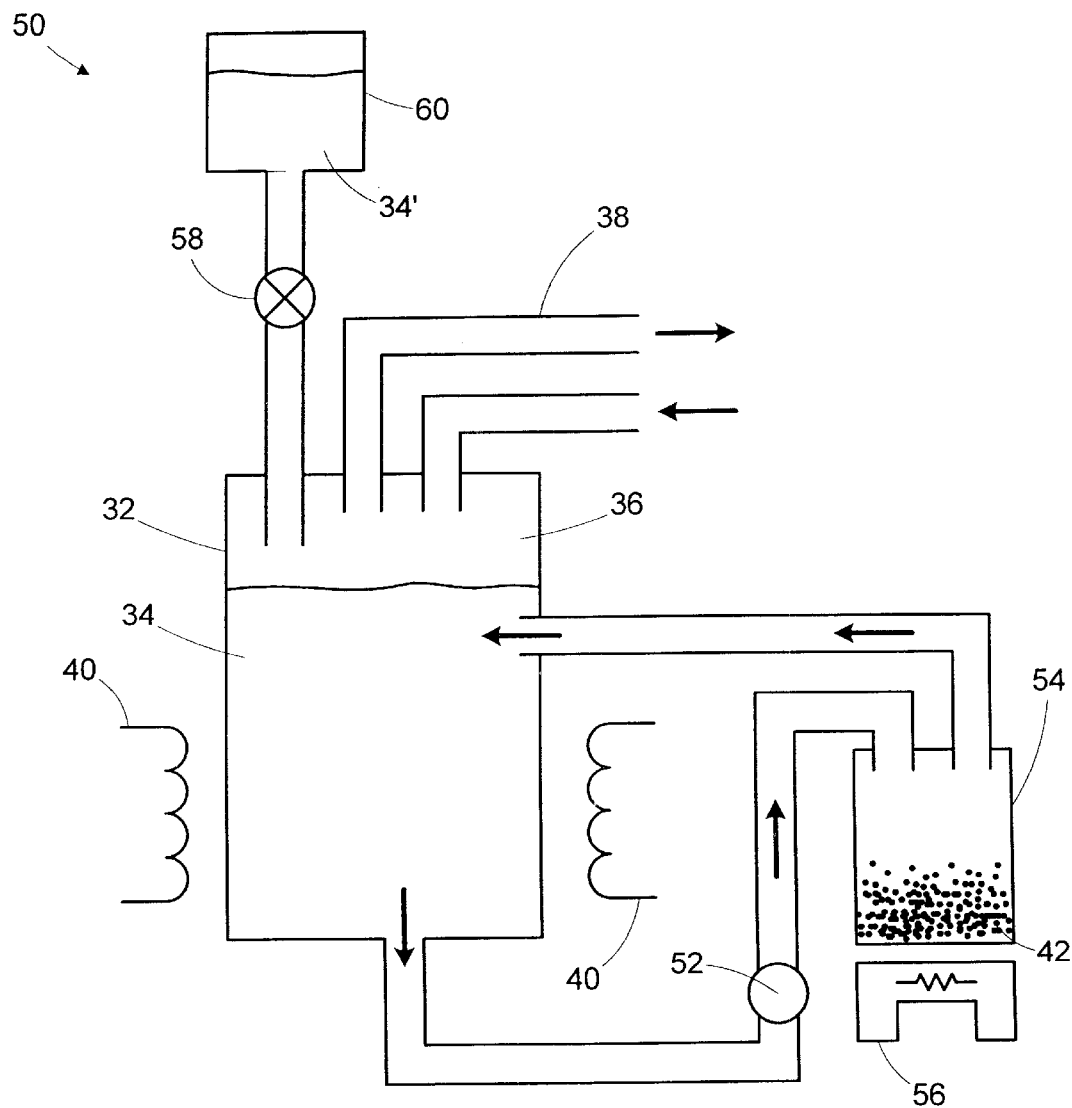
FIG. 4 illustrates a continuous type reactor used to produce the mixed constituent crystalline phase.

The disclosed process may also be performed in a continuous arrangement as shown schematically by the bioreactor 50 shown in FIG. 4. The bioreactor 50 operates in a similar manner as the bioreactor 30 of FIG. 3. The bioreactor 50 includes a fluid recirculator 52 that allows the culture medium 34 to pass through an external trap 54 from which the crystalline product 36 can be removed. The trap 54 may separate the crystalline product 42 from the circulating culture medium by settling, due to the greater density of the crystalline product 42. In many cases, the crystalline product 42 is magnetic, and the collection process can be assisted by using an electromagnet 56 or other suitable field producing device to provide a magnetic field gradient in the trap 54.

Continuous collection of product from the circulating fluid may also be used as a means of controlling particle size, because the particles tend to grow larger the longer they remain in the culture. An additional fluid valve 58 may be provided through which additional culture medium or nutrients 34 may be added from an external reservoir 60 while maintaining the anaerobic conditions within the container 32.

The composition of the culture medium 34 may be changed periodically in order to make crystalline products 42 of various selected compositions. The electron acceptor may be adjusted during the process, to make, for example, particles with a compositionally zoned or layered structure for special applications.

Although many of the examples described herein are directed to the formation of mixed ferrites, it is contemplated that the technique may be used to produce other mixed metal oxide compositions, particularly those that might benefit from low-temperature synthesis as described above.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

6.0 REFERENCES

Dunin-Borkowski, R. E., et al., "Magnetic Microstructure of Magnetotactic Bacteria by Electron Holography", *Science*, 282, pp.1868–70, (1998)

Liu, S. V., et al., "Thermophilic Fe(III)-Reducing Bacteria from the Deep Subsurface: The Evolutionary Implications", *Science*, 277, pp. 1106–09, (1997)

Lovley, D. R., *Annu. Rev. Microbiol.*, 47, p. 263 (1993);

Nealson, K. H. and D. Saffarini, D., *Annu. Rev. Microbiol.*, 48, p. 311, 1994 Rickard, 1969

Stapletonetal.,(1999)

Zhang, C. et al., "Enhancement of Fe(III), Co(III) and Cr(VI) Reduction at Elevated Temperatures and by a Thermophilic Bacterium", *Appl. Biochem. and Biotech.*, 57–58, pp.923–32, (1996)

Zhang, C. et al. "Physiochemical, mineralogical, and isotopic characterization of magnetiterich iron oxides formed by thermophilic iron-reducing bacteria", *Geochimica et Cosmochimica Acta*. Vol. 61 No. 21. pp. 4621–4632 (1997)

Zhang, C. et al., (1999)

What is claimed:

1. A method for producing mixed-oxide compounds, comprising:

providing a supply of thermophilic bacteria, said thermophilic bacteria adapted for reducing at least one transition metal ion;

providing ions of a first metal and ions of at least a second metal, at least one of said metals being a transition metal, said first metal being different from said second metal; and combining said thermophilic bacteria, said ions and at least one electron donor in a reactor at a temperature of from between about 25° C. and about 85° C. to reduce at least one of said ions through metabolic activity of said thermophilic bacteria;

wherein said thermophilic bacteria reduce said ions of at least one of said transition metals to form at least one mixed-oxide compound, said mixed-oxide compound comprising both said first and second metals.

2. The method of claim 1, wherein said electron donor is at least one selected from the group consisting of formate, glucose, acetate, lactate, pyruvate, and hydrogen.

3. The method of claim 2, wherein said electron donor is provided at a concentration from about 10 mM to about 70 mM.

4. The method of claim 2, wherein said hydrogen is provided to said reactor as a mixture of about 80% $H_2$/20% $CO_2$.

5. The method of claim 1, wherein said transition metal is selected from the group consisting of Fe(III), Cr(VI), Co(III), Ni(III), Mn(IV), U(VI), Ni(II), Al(III), Zn(II), Mg(II), Mn(II), Cu(II), Co(II), and Pd(II).

6. The method of claim 1, wherein said transition metal comprises Fe(III).

7. The method of claim 1, wherein said transition metal comprises Fe(III) oxyhydroxide.

8. The method of claim 1, wherein said thermophilic bacteria comprises at least one selected from the group consisting of Thermoanaerobacter and Thermoanaerobium bacteria.

9. The method of claim 8, wherein said thermophilic bacteria comprises at least one selected from the group consisting of TOR39, C1 and M3.

10. The method of claim 9, wherein said thermophilic bacteria comprises Thermoanaerobacter TOR39.

11. The method of claim 1, wherein said reactor temperature is from between about 45° C. and about 85° C.

12. The method of claim 1, wherein said reactor temperature is from between about 42° C. and about 65° C.

13. The method of claim 1, wherein said reactor temperature is from between about 65° C. and about 85° C.

14. The method of claim 1, wherein the pH of said reactor is from between about pH 6.2 and about pH 8.5.

15. The method of claim 1, wherein said reactor is held under anaerobic conditions.

16. The method of claim 1, wherein said mixed-oxide compound comprises a plurality of nanoparticles.

17. The method of claim 1, wherein ions of only one of said first and said second metal are reducible by said thermophilic bacteria.

18. The method of claim 1, wherein ions of both said first and said second metals are reducible by said thermophilic bacteria.

19. The method of claim 1, wherein said method proceeds for about 1 week to about 4 weeks.

20. The method of claim 1, further comprising obtaining said mixed-oxide compound from said reactor.

21. The method of claim 20, wherein said compound is obtained from said reactor by applying a magnetic field.

22. The method of claim 20, wherein said compound is obtained from said reactor by circulating said thermophilic bacteria through a trap, and collecting said compound from said trap.

23. The method of claim 1, wherein the ratio of said first and said second metals in said mixed-oxide compound is proportional to the ratio of said ions of said first and said second metal in said reactor.

24. A method for producing mixed-oxide compounds, comprising:

providing a supply of thermophilic bacteria, said thermophilic bacteria adapted for reducing at least one transition metal ion;

providing ions of a first reducible transition metal and ions of at least a second reducible transition metal, said first transition metal being different from said second transition metal; and combining said thermophilic bacteria, said ions and at least one electron donor in a reactor at a temperature of from between about 25° C. and about 85° C. to reduce at least one of said ions through metabolic activity of said thermophilic bacteria;

wherein said thermophilic bacteria reduce said ions of at least one of said transition metals to form said at least one mixed-oxide compound, said mixed-oxide compound comprising both said first and second transition metals.

25. The method of claim 24, wherein said first reducible transition metal comprises Fe(III).

26. A method for producing mixed-oxide compounds, comprising:

providing a supply of thermophilic bacteria, said thermophilic bacteria adapted for reducing at least one transition metal ion;

providing ions of a first reducible transition metal and ions of at least a second nonreducible transition metal, said first reducible transition metal being different from said second nonreducible transition metal; and combining said thermophilic bacteria, said ions and at least one electron donor in a reactor at a temperature of from between about 25° C. and about 85° C. to reduce at least one of said ions through metabolic activity of said thermophilic bacteria;

wherein said thermophilic bacteria reduce said ions of at least one of said transition metals to form at least one mixed-oxide compound, said mixed-oxide compound comprising both said first and second transition metals.

27. The method of claim 26, wherein said non-reducible transition metal comprises Zn(II).

* * * * *